United States Patent [19]

Cross et al.

[11] Patent Number: 5,340,831
[45] Date of Patent: Aug. 23, 1994

[54] MUSCARINIC RECEPTOR ANTAGONISTS

[75] Inventors: Peter E. Cross, Canterbury; Alexander R. MacKenzie, Deal, both of England

[73] Assignee: Pfizer Inc., New York, N.Y.

[21] Appl. No.: 859,471

[22] PCT Filed: Nov. 29, 1990

[86] PCT No.: PCT/EP90/02043
§ 371 Date: Jun. 12, 1992
§ 102(e) Date: Jun. 12, 1992

[87] PCT Pub. No.: WO91/09013
PCT Pub. No.: Jun. 21, 1991

[30] Foreign Application Priority Data

Dec. 12, 1989 [GB] United Kingdom ............ 8928042.4

[51] Int. Cl.$^5$ ..................... A61K 31/40; C07D 207/09
[52] U.S. Cl. ..................... 514/408; 514/428; 548/566; 548/568
[58] Field of Search .............. 514/408, 428; 548/566, 548/568

[56] References Cited

U.S. PATENT DOCUMENTS

| | | | |
|---|---|---|---|
| 4,810,713 | 3/1989 | Yanni et al. | 514/317 |
| 4,950,674 | 8/1990 | Yanni et al. | 514/317 |
| 5,096,890 | 3/1992 | Cross et al. | 548/568 X |
| 5,233,053 | 8/1993 | Cross et al. | 548/568 |

FOREIGN PATENT DOCUMENTS 0178946  4/1986  European Pat. Off. .
0235463  9/1987  European Pat. Off. .

OTHER PUBLICATIONS

D. E. Ames, *Synthesis of 1-(1-Methylpyrrolid-3-yl)-1,-1-diphenylbutan-2-one* J. Chem. Soc., (1960), pp. 2780-2781.

*Primary Examiner*—Joseph Paul Brust
*Attorney, Agent, or Firm*—Peter C. Richardson; Paul H. Ginsburg; Garth Butterfield

[57] ABSTRACT

Muscarinic receptor antagonists of formula (I), and their pharmaceutically acceptable salts, wherein Y is $-CH_2-$, $-(CH_2)_2-$, $-CH_2O-$, $-(CH_2)_2O-$ or $-CH_2S-$; R is $-CH$ or $-CONH_2$; and $R^1$ is a group of formula (a), where $R^2$ and $R^3$ are each independently H, $C_1-C_4$ alkyl, $C_1-C_4$ alkoxy, $-(CH_2)_nOH$, halo, trifluoromethyl, cyano, $-(CH_2)_nNR^4R^5$, $-CO(C_1-C_4$ alkyl), $-OCO(C_1-C_4$ alkyl), $-CH(OH)(C_1-C_4$ alkyl), $-C(OH)(C_1-C_4$ alkyl$_2$, $-SO_2NH_2$, $-(CH_2)_nCONR^6R^7$ or $-(CH_2)_nCOO(C_1-C_4$ alkyl); $R^4$ is H or $C_1-C_4$ alkyl; $R^5$ is H, $C_1-C_4$ alkyl or $C_1-C_4$ alkysulphonyl; $R^6$ and $R^7$ are each independently H or $C_1-C_4$ alkyl; and n is 0, 1 or 2. The compounds are particularly useful in treating irritable bowel syndrome.

6 Claims, No Drawings

MUSCARINIC RECEPTOR ANTAGONISTS

BACKGROUND OF THE INVENTION

This invention relates to certain 3-substituted pyrrolidine derivatives. The compounds of the invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

SUMMARY OF THE INVENTION

According to the invention there are provided compounds of the formula:

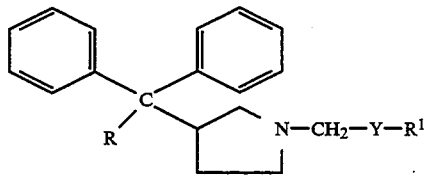

and their pharmaceutically acceptable salts, wherein
Y is $-CH_2-$, $-(CH_2)_2-$, $-CH_2-$, $-(CH_2)_2O-$ or $-CH_2S-$; R is $-CN$ or $-CONH_2$; and $R^1$ is a group of the formula:

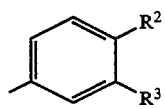

where
$R^2$ and $R^3$ are each independently H, $C_1-C_4$ alkyl, $C_1-C_4$ alkoxy, $-(CH_2)_n OH$, halo, trifluoromethyl, cyano, $-(CH_2)NR^4R^5$, $-CO(C_1-C_4$ alkyl), $-O-CO(C_1-C_4$ alkyl), $-CH(OH)(C_1-C_4$ alkyl), $-C(OH)(C_1-C_4$ alkyl)$_2$, $-SO_2NH_2$, $-(CH_2)_nCONR^6R^7$ or $-(CH_2)_nCOO(C_1-C_4$ alkyl);
$R^4$ is H or $C_1-C_4$ alkyl;
$R^5$ is H, $C_1-C_4$ alkyl or $C_1-C_4$ alkylsulphonyl;
$R^6$ and $R^7$ are each independently H or $C_1-C_4$ alkyl; and
n is 0, 1 or 2;

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy.

R is preferably $-CONH_2$. The compounds in which R is $-CN$ have some activity as muscarinic receptor antagonists but are mainly useful as synthetic intermediates.

Preferably $R^2$ and $R^3$ are each independently selected from H, halo, cyano, $C_1-C_4$ alkyl, $C_1-C_4$ alkoxy, $C_1-C_4$ alkoxycarbonyl, $C_1-C_4$ alkanesulphonamido, sulphamoyl, carbamoyl, hydroxymethyl, hydroxy and $-CO(C_1-C_4$ alkyl).

Y is preferably $-CH_2-$, $-(CH_2)_2-$, $-CH_2O-$ or $-(CH_2)_2O-$.

The anticholinergic activity of the present compounds resides in both the 3R-forms and 3S-forms, i.e., the compounds having R and S stereochemistry, respectively, at position 3 of the pyrrolidine ring, and of course in the 3R,S-(racemic) forms of the compounds (I). The 3S- forms are generally the most active.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1-19. These salts can be prepared conventionally, e.g. by mixing a solution of the free base and the acid in a suitable solvent, e.g. ethanol, and recovering the acid addition salt either as a precipitate, or by evaporation of the solution.

DETAILED DESCRIPTION OF THE INVENTION

The compounds of the formula (I) can be prepared by a number of routes, including the following:

Route A

This can be illustrated as follows:

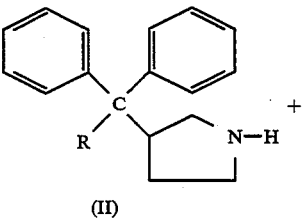

$Q-CH_2-Y-R^1 \longrightarrow$ Compounds (I)
(III)

Y, R and $R^1$ are as defined for formula (I) and Q is a leaving group, e.g. Br, Cl, I, $C_1-C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium bicarbonate, sodium or potassium carbonate, triethylamine or pyridine, and in a suitable organic solvent, e.g. acetonitrile, at up to the reflux temperature. Reaction temperatures of 60°-120° C. are generally desirable and it is most convenient to carry out the reaction under reflux. Iodo is often a particularly suitable leaving group but since the starting materials (III) are sometimes most conveniently available as chlorides the reaction can also be carried out using the compound (III) as a chloride but in the presence of an iodide such as sodium or potassium iodide. In the preferred technique, the compounds (II) and (III) are refluxed together in acetonitrile in the presence of potassium carbonate or sodium bicarbonate. The product (I) can be isolated and purified conventionally.

The 3R,S-, 3R- or 3S- forms of the starting material (II) are preferably used so as to obtain the 3R,S-, 3R- or 3S- forms of the product.

The starting materials of the formula (II) can be obtained by conventional procedures such as those described in the following Preparations section. The starting materials of the formula (III) are in general known compounds which can be prepared by conventional techniques. The preparation of any novel starting materials of the formula (III) used in the Examples is however described in the following Preparations section.

Route B

The compounds of the formula (I) in which R is —$CONH_2$ can be prepared by the hydrolysis of the corresponding nitriles, e.g. using concentrated aqueous mineral acid (typically concentrated aqueous $H_2SO_4$).

The hydrolysis is typically carried out using concentrated aqueous sulphuric acid, preferably 80-98% sulphuric acid and most preferably 90% $H_2SO_4$, with heating at e.g. 80°-110° C. and most preferably at about 100° C. The product can then be isolated and purified by conventional procedures. Clearly any cyano substituents on $R^1$ are also likely to be hydrolysed to carbamoyl or carboxy, any alkanoyloxy substituents to hydroxy, and any alkoxycarbonyl substituents to carboxy.

Some of the compounds of the formula (I) in which $R^1$ is a substituted phenyl group can be converted to other compounds of the formula (I) as follows:

(a) When R is —$CONH_2$, a —$CO_2(C_1-C_4$ alkyl) substituent on the phenyl group can be selectively reduced to —$CH_2OH$. Lithium aluminium hydride is the most suitable reducing agent. The reaction is typically carried in a suitable organic solvent, e.g. ether, at between 0° and room temperature. It is generally most convenient to use the starting material in the form of its methyl ester.

(b) A hydroxy substituent on the phenyl group can be converted to —$OCO(C_1-C_4$ alkyl) by acylation using a $C_1-C_4$ alkanoyl chloride or bromide, or an alkanoic arthydride of the formula ($C_1-C_4$ alkyl. $CO)_2O$. The presence of an acid acceptor is preferable. The reaction is typically carried out at about room temperature in a suitable organic solvent, e.g. dioxan.

(c) A —$CO(C_1-C_4$ alkyl) substituent on the phenyl group can be reduced to a substituent of the formula —$CH(OH)(C_1-C_4$ alkyl). A suitable reducing agent is sodium borohydride. The reaction is typically carried out at between 0° and room temperature in a suitable organic solvent, e.g. methanol.

(d) When R is —$CONH_2$, a —$(CH_2)_nCOO(C_1-C_4$ alkyl) substituent, preferably where the alkyl group is methyl, can be converted to —$(CH_2)_nCONR^6R^7$ by reaction with ammonia or the appropriate amine $R^6R^7NH$. When $R^6$ and $R^7$ are both H, the use of aqueous (0.880) ammonia is generally most convenient, although the reaction can be carried out using ammonia in an organic solvent such as methanol or ethanol, or ammonia neat in a bomb. The reaction with methylamine is most conveniently carried out in ethanol. Although in some instances the reaction may proceed at a satisfactory rate at room temperature, heating at up to 120°, preferably 60° to 100° C., is generally necessary. For volatile amines, the reaction is best carried out in a bomb.

(e) A hydroxy substituent can be converted to $C_1-C_4$ alkoxy firstly by reaction with a base such as potassium carbonate, and secondly by reaction with a $C_1-C_4$ alkyl iodide or bromide. The reaction is typically carried out in a solvent such as dioxan or acetone, and preferably under reflux.

(f) A hydroxymethyl or hydroxyethyl substituent on the phenyl group can be converted to —$CH_2NR^4R^5$ or —$(CH_2)_2NR^4R^5$ firstly by reaction with thionyl chloride and secondly by reaction with ammonia or the appropriate amine $R^4R^5NH$, $R^4$ and $R^5$ each being H or $C_1-C_4$ alkyl. The reaction with thionyl chloride is typically carried out with heating, preferably under reflux, in a solvent such as methylene chloride. The reaction with ammonia or the amine is typically carried out at in a solvent such as ethanol, and heating, e.g. under reflux, may be necessary.

(g) When R is —$CONH_2$, a —$CO(C_1-C_4$ alkyl) substituent can be converted to —$C(OH)(C_1-C_4$ alkyl)$_2$ by reaction with a $C_1-C_4$ alkyllithium or $C_1-C_4$ alkylmagnesium bromide, chloride, or iodide (e.g. methyllithium, methylmagnesium bromide, methylmagnesium iodide or methylmagnesium chloride). The reaction is typically carried out in a solvent such as ether at a temperature of from 0° C. to room temperature. and (h) An iodo substituent can be converted to $C_1-C_4$ alkoxycarbonyl by reaction, typically at about room temperature, with carbon monoxide in a $C_1-C_4$ alkanol containing a base [e.g. potassium carbonate] and a palladium (II) catalyst [e.g. bis(triphenylphosphine)palladium (II) chloride].

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea and right atrium) are determined using a 1-5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined (p$A_2$ value—Arunlakshana and Schild (1959), Brit. J. Pharmacol., 14, 48–58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the sailration and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to B5 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes a method of treatment of a human being to cure or prevent a disease associated with the altered motility and/or tone of smooth muscle, such as irritable bowel syndrome, which comprises treating said human being with an effective amount of a compound of the formula (I), or a pharmaceutically acceptable salt or composition thereof.

The following Examples, in which all temperatures are in °C., illustrate the invention:

EXAMPLE 1

Preparation of 3-(R,S)-(1-carbamoyl-1,1-diphenylmethyl)-1l-(4-methanesulphonamidophenethyl)pyrrolidine

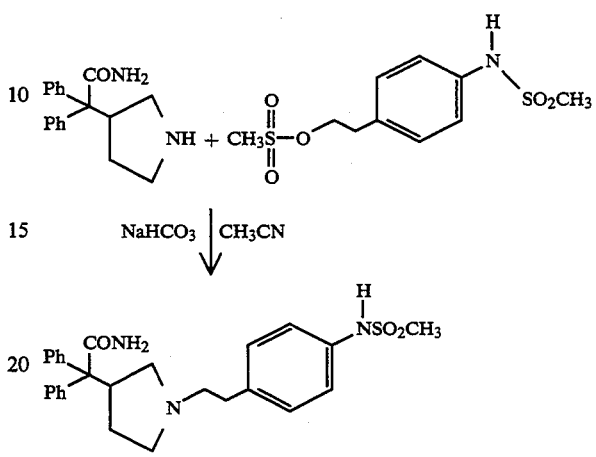

A mixture containing 3-(R,S)-(1-carbamoyl-1,1-diphenylmethyl)pyrrolidine (0.5 g - see Preparation 8), N-[4-(2-methanesulphonyloxyethyl)phenyl]methanesulphonamide (0.5 g—see Preparation 12), sodium bicarbonate (0.5 g) and acetonitrile (20 ml) was heated under reflux for 2 hours. On cooling to room temperature, water (60 ml) was added and the mixture was extracted with dichloromethane (3×50 ml). The combined dichloromethane extracts were dried ($MgSO_4$) and concentrated in vacuo to give an oil which was purified by column chromatography on silica eluting with dichloromethane containing methanol (2% up to 10%). The product-containing fractions were combined and concentrated in vacuo to give the title compound as a colourless foam, yield, 0.1g.

Analysis %: Found C,60.61; H,6.29; N,8.41; Calculated for $C_{27}H_{31}N_3O_3S.3/2\ H_2O.\frac{1}{2}CH_2Cl_2$: C,60.47; H,6.62; N,7.90.

$^1$H-N.M.R. ($d^6$ DMSO+$CF_3CO_2D$)δ=7.45–7.10 (m, 14H); 4.00–3.70 (m, 2H); 3.50–3.25 (m, 3H); 3.20–3.05 (m, 1H); 3.00–2.70 (m, 2H); 2.90 (s, 3H); 2.65–2.30 (m, 1H); 2.20–2.10 (m, 1H); 1.70–1.40 (m, 1H) ppm.

EXAMPLE 2

Preparation of 3-(R,S)-(1-carbamoyl-1,1-diphenylmethyl)-1-(3,4-dimethylphenethyl)pyrrolidine

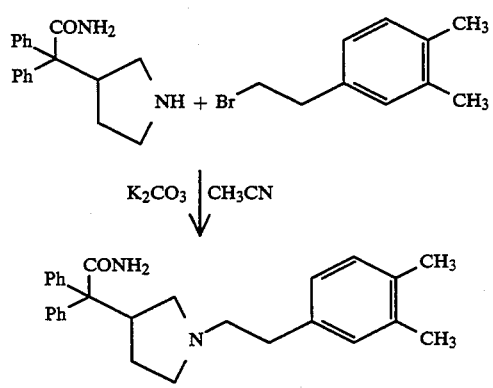

A mixture containing 3-(R,S)-(1-carbamoyl-1,1-diphenylmethyl)pyrrolidine (0.5 g—see Preparation 8), 3,4-dimethylphenethyl bromide (0.4 g—see Preparation 18), anhydrous potassium carbonate (0.5 g) and acetonitrile (10 ml) was heated under reflux for 2 hours. On cooling to room temperature, water (80 ml) was added and the mixture was extracted with dichloromethane (3×70 ml). The combined dichloromethane extracts were dried (MgSO₄) and concentrated in vacuo to give a yellow oil which was purified by column chromatography on silica eluting with dichloromethane containing methanol (0% up to 4%). The product-containing fractions were combined and concentrated in vacuo to give the title compound as an oil, yield, 0.22 g.

Analysis %: Found C,78.21; H,7.57; N,6.65; Calculated for $C_{28}H_{32}N_2O \cdot H_2O$: C,78.09; H,7.95; N,6.51.

¹H-N.M.R. (CDCl₃)δ =7.45–7.15 (m, 11H); 7.10–6.90 (m, 3H); 5.40–5.30 (brs, 1H); 3.60–3.45 (m, 2H); 3.00–2.40 (m, 7H); 2.25 (s, 6H); 2.10–1.95 (m, 2H) ppm.

EXAMPLE 3

Preparation of 3-(R,S)-(1-carbamoyl-1,1-diphenylmethyl)-1-(4-fluorophenethyl)pyrrolidine

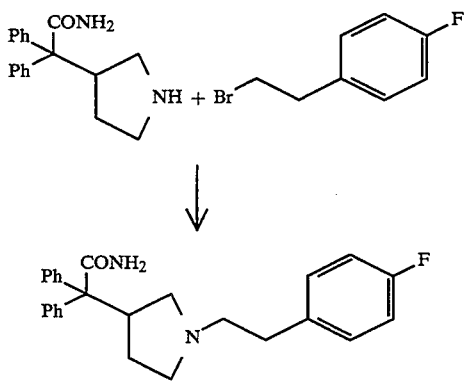

A mixture containing 3-(R,S)-(1-carbamoyl-1,1-diphenylmethyl)pyrrolidine (0.5 g—see Preparation 8), 4-fluorophenethyl bromide (0.36 g—see J.A.C.S., 63, 602 (1941)), anhydrous potassium carbonate (0.5 g) and acetonitrile (15 ml) was heated under reflux for 2 hours. On cooling to room temperature, water (70 ml) was added and the mixture was extracted with dichloromethane (3×50 ml). The combined dichloromethane extracts were dried (MgSO₄) and concentrated in vacuo to give a glass which was purified by column chromatography on silica eluting with dichloromethane containing methanol (2% up to 4%). The product-containing fractions were combined and concentrated in vacuo to give the title compound as a colourless glass, yield, 0.056 g.

Analysis %: Found: C,76.19; H,6.76; N,7.05; Calculated for $C_{26}H_{27}FN_2O \cdot \frac{1}{2}H_2O$: C,75.88; H,6.86; N,6.81.

¹H-N.M.R. (CDCl₃)δ=7.60–6.90 (m, 15H); 5.45–5.30 (brs, 1H); 3.55–3.40 (m, 1H); 2.95–2.45 (m, 8H); 2.10–1.90 (m, 2H) ppm.

EXAMPLE 4

Preparation of 3-(R,S)-(1-carbamoyl-1,1-diphenylmethyl)-1-(3-methylphenethyl)pyrrolidine

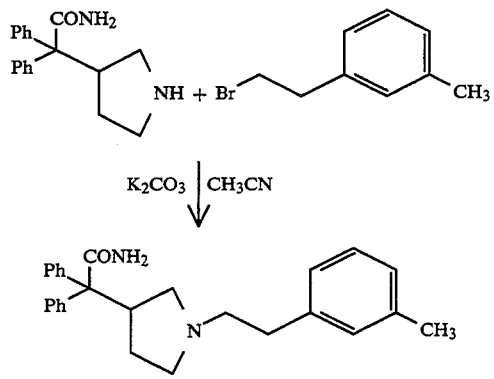

A mixture containing 3-(R,S)-(1-carbamoyl-1,1-diphenylmethyl)pyrrolidine (0.5 g—see Preparation 8), 3-methylphenethylbromide (0.36 g—see J. Ind. Chem. Sac., 40, 327, (1963)), anhydrous potassium carbonate (0.5 g) and acetonitrile (10 ml) was heated under reflux for 4 hours. On cooling to room temperature, water (60 ml) was added and the mixture was extracted with dichloromethane (3×50 ml). The combined dichloromethane extracts were dried (MgSO₄) and concentrated in vacuo to give an oil which was purified by column chromatography on silica eluting with dichloromethane containing methanol (2% up to 4%). The product-containing fractions were combined and concentrated in vacuo to give the title compound as an oil, yield, 0.17 g.

Analysis %: Found C,79.76; H,7.48; N,7.04; Calculated for $C_{27}H_{30}N_2O \cdot \frac{1}{2}H_2O$: C,79.56; H,7.66; N,6.87.

¹H-N.M.R. (CDCl₃)δ=7.95–7.75 (brs, 1H), 7.50–7.10 (m, 11H); 7.05–6.90 (m, 3H); 5.35–5.25 (brs, 1H); 3.50–3.40 (m, 1H); 3.00–2.65 (m, 7H); 2.55–2.40 (m, 1H); 2.35 (s, 3H); 2.10–1.90 (m, 2H) ppm.

EXAMPLE 5

Preparation of 3-(R,S)-(1-carbamoyl-1,1-diphenylmethyl)-1-(4-sulphamoylphenethyl)pyrrolidine

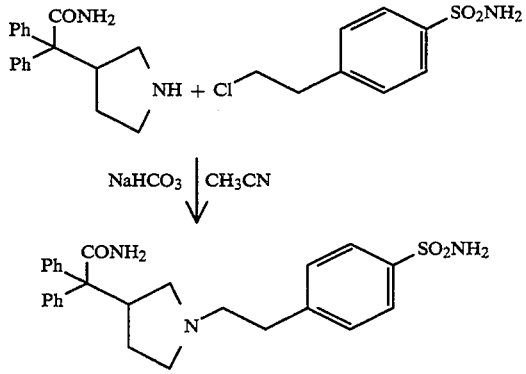

A mixture containing 3-(R,S)-(1-carbamoyl-1,1-diphenylmethyl)pyrrolidine (0.3 g—see Preparation 8), 4-sulphamoylphenethyl chloride (0.23 g—see J. Pharm. Pharmacol., 16, 541, (1964)), sodium bicarbonate (0.4 g)

and acetonitrile (10 ml) was heated under reflux for 2 hours. A further portion of sodium bicarbonate (1 g) was added followed by potassium iodide (0.2 g) and the mixture was heated under reflux for 2 hours. On cooling to room temperature, water (60 ml) was added and the mixture was extracted with dichloromethane (3×50 ml). The combined dichloromethane extracts were dried (MgSO4) and concentrated in vacuo to give a glass which was purified by column chromatography on silica eluting with dichloromethane containing methanol (0% up to 10%). The product-containing fractions were combined and concentrated in vacuo to give the title compound as a colourless foam, yield, 0.11 g.

Analysis %: Found C,60.24; H,5.76; N,7.78; Calculated for $C_{26}H_{29}N_3O_3S.H_2O\frac{1}{2}CH_2Cl_2$: C,60.73; H,6.15; N,8.01.

$^1$H-N.M.R. (CDCl$_3$)$\delta$=7.70 (d, 2H); 7.40–7.20 (m, 13H); 7.15 (brs, 1H); 7.00 (brs, 1H); 5.75 (s, 1H); 3.70–3.60 (m, 1H); 2.95–2.85 (m, 1H); 2.70–2.35 (m, 6H); 2.00–1.85 (m, 2H); 1.60–1.45 (m, 1H) ppm.

EXAMPLE 6

Preparation of 3-(R,S)=(1-carbamoyl-1-1-diphenylmethyl)-1-(3-phenylpropyl)pyrrolidine

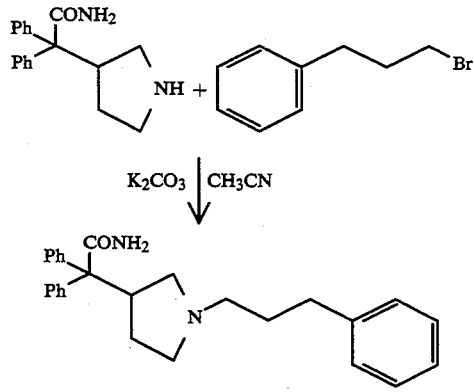

A mixture containing 3-(R,S)-(1-carbamoyl-1,1-diphenyl-methyl)pyrrolidine (0.3 g—see Preparation 8), 1-bromo-3-phenylpropane (0.22 g), anhydrous potassium carbonate (0.4 g) and acetonitrile (10 ml) was heated under reflux for 2 hours. On cooling to room temperature, water (40 ml) was added and the mixture extracted with dichloromethane (3×50 ml). The combined dichloromethane extracts were dried (MgSO4) and concentrated in vacuo to give an oil which was purified by column chromatography on silica eluting with dichloromethane containing methanol (2% up to 10%). The product-containing fractions were combined and concentrated in vacuo to give the title compound as an oil, yield, 0.19 g.

Analysis %: Found C,75.31; H,7.04; N,6.66; Calculated for $C_{27}H_{30}N_2O.H_2O.1/5\ CH_2Cl_2$: C,75.35; H,7.52; N,6.46.

$^1$H-N.M.R. (CDCl$_3$)$\delta$=7.40–7.00 (m, 17H); 3.80–3.65 (m, 1H); 3.10–2.90 (m, 1H); 2.70–1.80 (m, 8H); 1.70–1.50 (m, 3H) ppm.

EXAMPLE 7

Preparation of 3-(R,S)-(1-carbamoyl-1,1-diphenylmethyl)-1-(4-cyanophenethyl)pyrrolidine

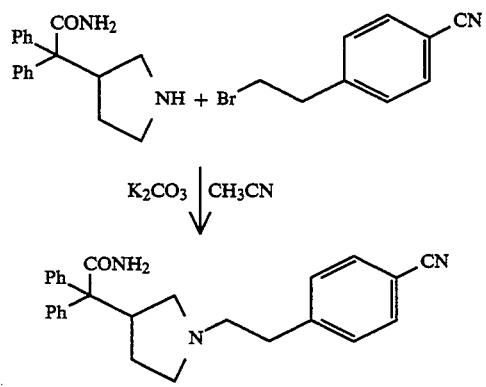

A mixture containing 3-(R,S)-(1-carbamoyl-1,1-diphenylmethyl)pyrrolidine (0.6 g—g see Preparation 13), anhydrous potassium carbonate (0.5 g) and acetonitrile (20 ml) was heated under reflux for 1.5 hours. On cooling to room temperature, water (60 ml) was added and the mixture extracted with dichloromethane (3×50 ml). The combined dichloromethane extracts were dried (MgSO4) and concentrated in vacuo to give a gum which was purified by column chromatography on silica eluting with dichloromethane containing methanol (0% up to 6%). The product-containing fractions were combined and concentrated in vacuo to give the title compound as a colourless foam, yield, 0.25 g.

Analysis %: Found: C,79.38; H,6.86; N,9.58; Calculated for $C_{27}H_{27}N_3O$: C,79.18; H,6.64; N,10.26.

$^1$H-N.M.R. (CDCl$_3$)$\delta$=7.65–7.55 (d, 2H); 7.45–7.15 (m, 12H); 6.90–6.75 (brs, 1H); 5.55–5.45 (brs, 1H); 3.60–3.34 (m, 1J); 2.90–2.50 (m, 8H); 2.15–1.90 (m, 2H) ppm.

EXAMPLE 8

Preparation of 3-(R,S)-(1-carbamoyl-1,1-diphenylmethyl)-1-(4-carbamoylphenethyl)pyrrolidine

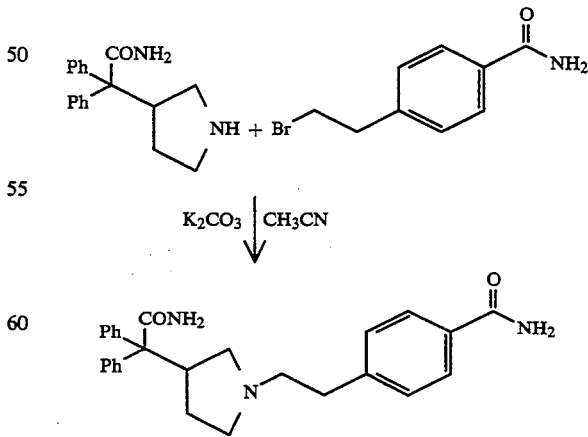

A mixture containing 3-(R,S)-(1-carbamoyl-1,1-diphenylmethyl)pyrrolidine (0.3 g—see Preparation 8), 4-carbamoylphenethyl bromide (0.25 g—see Preparation 13), anhydrous potassium carbonate (0.4 g) and acetonitrile (10 ml) was heated under reflux for 5 hours. On cooling to room temperature, water (40 ml) was added and the resulting mixture extracted with dichloromethane (3×30 ml). The combined dichloromethane extracts were dried (MgSO4) and concentrated in vacuo to give a yellow foam which was purified by column chromatography on silica eluting with dichloromethane containing methanol (0% up to 10%). The product-containing fractions were combined and concentrated in vacuo to give the title compound as a colourless foam, yield, 0.13 g.

Analysis %: Found: C,72.06; H,6.69; N,8.55; Calculated for $C_{27}H_{29}N_3O_2.\frac{1}{8}CH_2CL_2$: C,72.01; H,6.56; N,9.21;

1H-N.M.R. (CDCl3)δ=7.80–7.70 (d, 2H); 7.50–7.20 (m, 13H); 6.25–6.05 (brs, 1H); 5.85–5.65 (brs, 1H); 5.60–5.50 (brs, 1H); 3.55–3.40 (m, 1H); 2.95–2.65 (m, 7H); 2.55–2.45 (m, 1H); 2.05–1.95 (m, 2H) ppm.

EXAMPLE 9

Preparation of 3-(R,S)-(1-carbamoyl-1,1-diphenylmethyl)-1-(3-phenoxypropyl)pyrrolidine

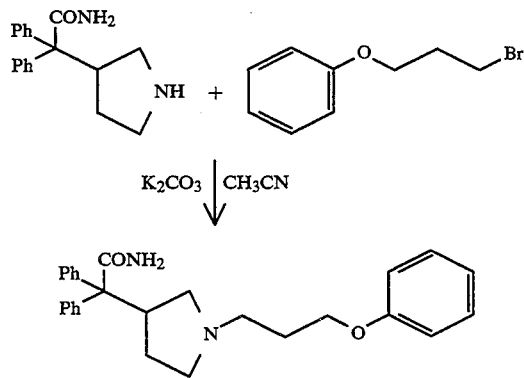

A mixture containing 3-(R,S)-(1-carbamoyl-1,1-diphenylmethyl)pyrrolidine (0.3 g—see Preparation B), 3-phenoxypropylbromide (0.24 g), anhydrous potassium carbonate (0.4 g) and acetonitrile (10 ml) was heated under reflux for 5 hours. On cooling to room temperature water (40 ml) was added and the resulting mixture extracted with dichloromethane (3×50 ml). The combined dichloromethane extracts were dried (MgSO4) and concentrated in vacuo to give an oil which was purified by column chromatography on silica eluting with dichloromethane containing methanol (0% up to 7%). The product-containing fractions were combined and concentrated in vacuo to give the title compound as a colourless foam, yield, 0.23 g.

Analysis %: Found C,74.94; H,7.1; N,6.41; Calculated for $C_{27}H_{30}N_2O_2.H_2O$: C,74.97; H,7.45; N,6.47.

1H-N.M.R. (CDCl3)δ=7.50–7.20 (m, 13H); 7.00–6.95 (t, 1H); 6.95–6.85 (d, 2H); 5.70–5.60 (brs, 1H); 4.05–3.95 (t, 2H); 3.70–3.55 (m, 1H); 3.05–2.85 (m, 2H); 2.85–2.60 (m, 4H); 2.25–1.95 (m, 4H) ppm.

EXAMPLE 10

Preparation of 3-(R,S)-(1-carbamoyl-1,1-diphenylmethyl)-1-(3,4-dichlorophenethyl)pyrrolidine

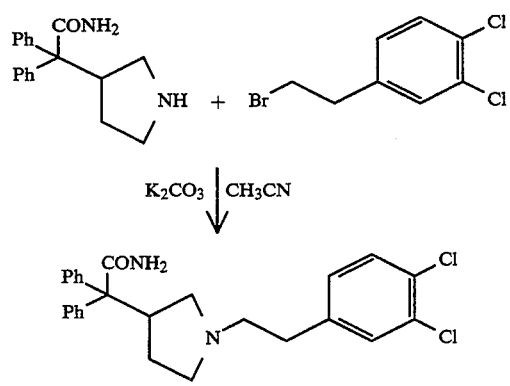

A mixture containing 3-(R,S)-(1-carbamoyl-1,1-diphenylmethyl)pyrrolidine (0.3 g—see Preparation 8), 3,4-dichlorophenethyl bromide (0.27 g—see Preparation 14), anhydrous potassium carbonate (0.4 g) and acetonltrile (10 ml) was heated under reflux for 4 hours. On cooling to room temperature, water (40 ml) was added and the resulting mixture extracted with dichloromethane (3×30 ml). The combined dichloromethane extracts were dried (MgSO4) and concentrated in vacuo to give a foam which was purified by column chromatography on silica eluting with dichloromethane containing methanol (0% up to 7%). The product-containing fractions were combined and concentrated in vacuo to give the title compound as a colourless foam, yield, 0.22 g.

Analysis %: Found C,70.41; H,6.05; N,5.82; Calculated for $C_{26}H_{26}Cl_2N_2O.H_2O$: C,70.13; H,6.33; N,6.29.

1H-N.M.R. (CDCl3)δ=7.45–7.05 (m, 13H); 7.05–7.00 (d, 1H); 5.55–5.40 (brs, 1H); 3.60–3.45 (m, 1H); 2.90–2.45 (m, 8H); 2.10–1.90 (m, 2H) ppm.

EXAMPLE 11

Preparation of 3-(R,S)-(1-carbamoyl-1,1-diphenylmethyl) -1-(4methoxycarbonylphenethyl)pyrrolidine

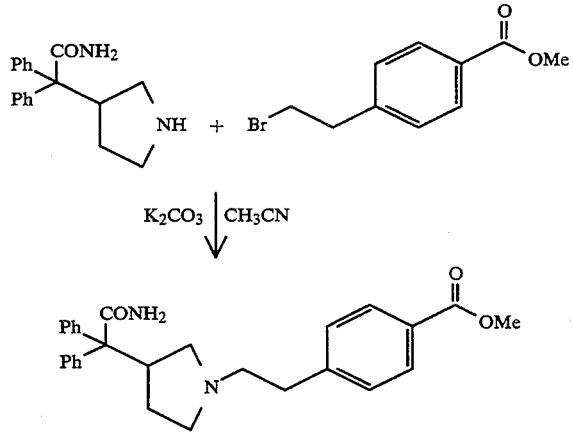

A mixture containing 3-(R,S)-(1-carbamoyl-1,1-diphenylmethyl)pyrrolidine (0.6 g—see Preparation 8), 4-methoxycarbonylphenethyl bromide (0.53 g—see Preparation 15), anhydrous potassium carbonate (0.5 g) and acetonitrile (20 ml) was heated under reflux for 1.5 hours. On cooling to room temperature, water (60 ml) was added and the resulting mixture extracted with dichloromethane (3×50 ml). The combined dichloromethane extracts were dried (MgSO$_4$) and concentrated in vacuo to give a gum which was purified by column chromatography on silica eluting with dichloromethane containing methanol (2% up to 6%). The product-containing fractions were combined and concentrated in vacuo to give the title compound as a colourless foam, yield, 0.44 g.

Analysis %: Found C,75.34; H,7.04; N,6.19; Calculated for $C_{28}H_{30}N_2O_3.1/20$ $CH_2Cl_2$: C,75.27; H,6.77; N,6.27.

$^1$H-N.M.R. (CDCl$_3$)δ=8.00–7.95 (d, 2H); 7.55–7.15 (m, 13H); 5.35–5.25 (brs, 1H); 3.95 (s, 3H); 3.55–3.40 (m, 1H); 2.95–2.65 (m, 7H); 2.55–2.45 (m, 1H); 2.05–1.90 (m, 2H) ppm.

EXAMPLE 12

Preparation of 3-(R,S)-(1-carbamoyl-1,1-diphenylmethyl)-1-(2-phenoxyethyl)pyrrolidine

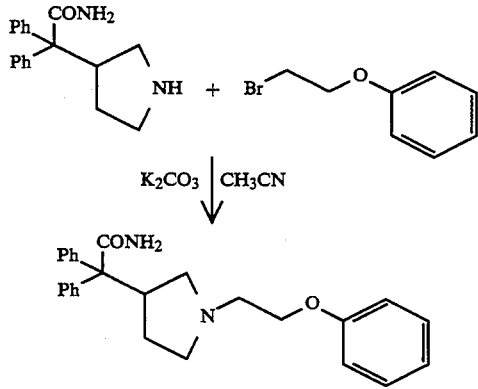

A mixture containing 3-(R,S)-(1-carbamoyl-1,1-diphenylmethyl)pyrrolidine (0.25 g—see Preparation 8), 2-phenoxyethyl bromide (0.18 g), anhydrous potassium carbonate (0.3 g) and acetonitrile (10 ml) was heated under reflux for 1.5 hours. On cooling to room temperature, water (60 ml) was added and the mixture extracted with dichloromethane (3×50 ml). The combined dichloromethane extracts were dried (MgSO$_4$) and concentrated vacuo to give a foam which was purified by column chromatography on silica eluting with dichloromethane containing methanol (0% up to 6%). The product-containing fractions were combined and concentrated in vacuo to give the title compound as a colourless foam, yield, 0.18 g.

Analysis %: Found: C,76.71; H,6.97; N,7.03; Calculated for $C_{26}H_{28}N_2O_2.1/10$ $CH_2Cl_2$: C,76.50; H,6.91; N,6.85.

$^1$H-N.M.R. (CDCl$_3$)δ=7.60–7.20 (m, 13H); 7.00–6.90 (t, 1H); 6.85 (d, 2H); 5.65–5.55 (brs, 1H); 4.10–4.00 (t, 2H); 3.60–3.45 (m, 1H); 3.00–2.60 (m, 6H); 2.10–1.95 (m, 2H) ppm.

EXAMPLE 13

Preparation of 3-(S)-(−)-(1-carbamoyl-1-diphenylmethyl)-1-(3,4-dimethoxyphenethyl)pyrrolidine

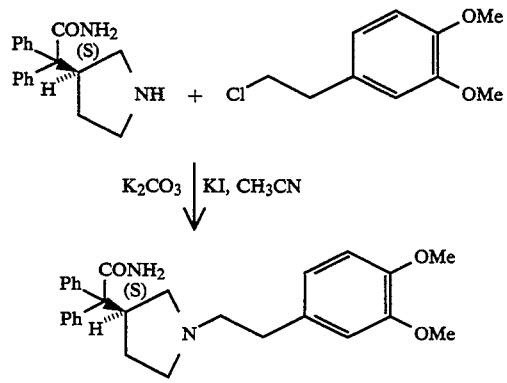

A mixture containing 3-(S)-(+)-(1-carbamoyl-1,1-diphenylmethyl)pyrrolidine-L-(+)-tartrate (0.4 g—see Preparation 10), 3,4-dimethoxyphenethyl chloride (0.21 g—see Org. Prep. Proced. Int., 10, 267 , (1978)), anhydrous potassium carbonate (0.3 g) , potassium iodide (0.17 g) and acetonitrile (10 ml) was heated under reflux for 18 hours. On cooling to room temperature, water (25 ml) was added and the mixture extracted with dichloromethane (3×30 ml). The combined dichloromethane extracts were dried (MgSO$_4$) and concentrated in vacuo to give a gum which was purified by column chromatography on silica eluting with dichloromethane containing methanol (0% up to 10%). The product-containing fractions were combined and concentrated in vacuo to give the title compound as a colourless foam, yield, 0.21 g, $[\alpha]^{25}_D$ −19.6° (c 1.0, $CH_2Cl_2$).

Analysis %: Found: C,72.94; H,6.99; N,6.24; Calculated for $C_{28}H_{32}N_2O_3.1/4$ $CH_2Cl_2$: C,73.07; H,6.98; N,6.04.

$^1$H-N.M.R. (CDCl$_3$)δ=7.80–7.20 (m, 11H); 6.85–6.70 (m, 3H); 5.40–5.30 (brs, 1H); 3.90 (s, 6H); 3.55–3.45 (brs, 1H); 3.00–2.65 (m, 8H); 2.10–1.90 (brm, 2H) ppm.

EXAMPLE 14

Preparation of 3-(S)-(-)-(1-carbamoyl-1,-diphenylmethyl)-1-(4-hydroxymethylphenethyl)pyrrolidine

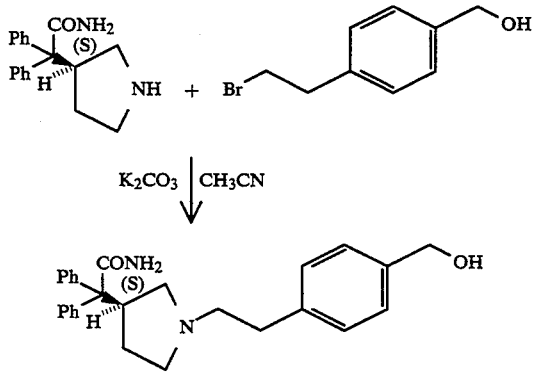

A mixture containing 3-(S)-(+)-(1-carbamoyl-1,1-diphenylmethyl)pyrrolidine-L-(+)-tartrate (0.4 g - see Preparation 10, 4-hydroxymethylphenethyl bromide (0.2 g—see U.S. Pat. No. 4,595,690), anhydrous potassium carbonate (0.2 g) and acetonitrile (10 ml) was heated under reflux for 15 hours. On cooling to room temperature, water (20 ml) was added and the layers separated. The aqueous layer was extracted with dichloromethane (3×20 ml), the extracts combined, dried (MgSO4) and concentrated in vacuo to give a foam. The foam was purified by column chromatography on silica eluting with dichloromethane containing methanol (0% up to 6%). The product-containing fractions were combined and concentrated in vacuo to give the title compound as a colourless foam, yield, 0.2 g, $[\alpha]^{25}_D -26.1°$ (c 1.0, CH2Cl2).

Analysis %: Found: C,76.22; H,7.38; N,6.38; Calculated for $C_{27}H_{30}N_2O_2.\frac{1}{4}H_2O.\frac{1}{8}Pr^i_2O$: C,75.62; H 7.75; N,6.12.

$^1$H-N.M.R. (CDCl3),δ=7.80–7.10 (m, 16H); 5.50–5.35 (brs, 1B); 4.65 (s, 2H); 3.55–3.40 (m, 1H); 2.95–2.40 (m, 8H); 2.10–1.90 (m, 2H) ppm.

EXAMPLE 15

Preparation of 3-(R,S)-(1-carbamoyl-1,1-diphenylmethyl)-1-phenethylpyrrolidine

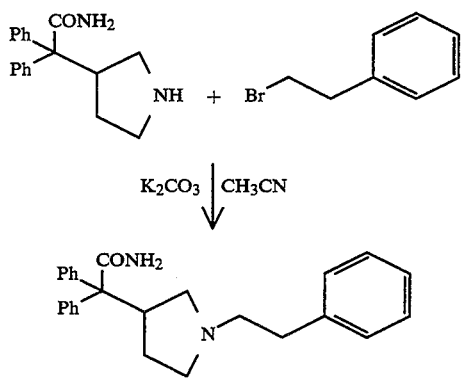

A mixture containing 3-(R,S)-(1-carbamoyl-1,1-diphenylmethyl)pyrrolidine (0.6 g—see Preparation 8), phenethyl bromide (0.4 g), anhydrous potassium carbonate (0.6 g) and acetonitrile (20 ml) was heated under reflux for 1.25 hours. The mixture was partitioned between 10% aqueous potassium carbonate (20 ml) and dichloromethane (50 ml), the layers were separated, and the aqueous layer extracted with dichloromethane (3×50 ml). The combined dichloromethane extracts were dried (MgSO4) and concentrated in vacuo to give an oil which was purified by column chromatography on silica eluting with dichloromethane containing methanol (0% up to 4%). The product-containing fractions were combined and concentrated in vacuo to give a foam which was crystallised from diisopropyl ether to give the title compound, yield, 0.21 g, m.p. 124°–129° C.

Analysis %: Found: C,81.13; H,7.51; N,7.07; Calculated for $C_{26}H_{28}N_2O$: C,81.21; H,7.34; N,7.29.

$^1$H-N.M.R. (CDCl3), δ=8.00–7.80 (brs, 1H); 7.50–7.10 (m, 15H); 5.30–5.10 (brs, 1H); 3.50–3.35 (m, 1H); 3.00–2.65 (m, 7H); 2.50–2.35 (m, 1H); 2.10–1.85 (m, 2H) ppm.

EXAMPLE 16

Preparation of 3-(R,S)-(1-carbamoyl-1,1-diphenylmethyl)-1-(4-methylphenethyl)pyrrolidine

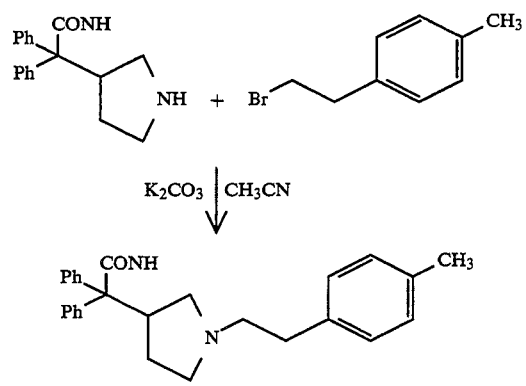

A mixture containing 3-(R,S)-(1-carbamoyl-1,1-diphenylmethyl)pyrrolidine (0.6 g—see Preparation 8), 4-methylphenethyl bromide (0.44 g), anhydrous potassium carbonate (0.6 g) and acetonitrile (20 ml) was heated under reflux for 1.25 hours. The mixture was partitioned between 10% aqueous potassium carbonate (10 ml) and dichloromethane (20 ml), the layers were separated, and the aqueous layer extracted with dichloromethane (3×20 ml). The combined dichloromethane extracts were dried (MgSO4) and concentrated in vacuo to give a gum which was purified by column chromatography on silica eluting with dichloromethane containing methanol (0% up to 6%). The product-containing fractions were combined and concentrated in vacuo to give the title compound as a colourless foam, yield, 0.32 g.

Analysis %: Found C,80.28; H,7.80; N,6.62; Calculated for $C_{27}H_{30}N_2O.\frac{1}{2}H_2O$: C,80.45; H,7.63; N,6.95.

$^1$H-N.M.R. (CDCl3) δ=7.95–7.70 (brs, 1H); 7.50–7.15 (m, 10H); 7.15–7.00 (ABq, 4H); 5.45–5.30 (brs, 1H); 3.50–3.40 (m, 1H); 3.00–2.65 (m, 7H); 2.55–2.40 (m, 1H); 2.35 (s, 3H); 2.05–1.90 (m, 2H) ppm.

EXAMPLE 17

(A) Preparation of 3-(R,S)-(1-carbamoyl-1,1-diphenylmethyl)-1-(4-chlorophenethyl)pyrrolidine

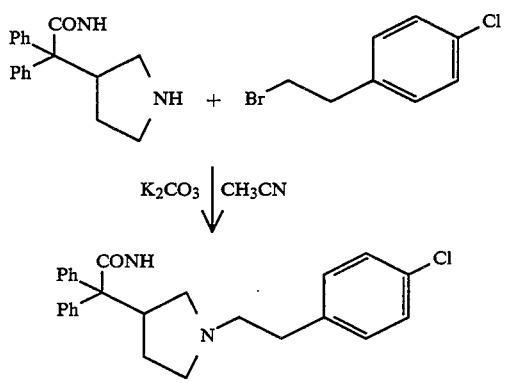

A mixture containing 3-(R,S)-(1-carbamoyl-1,1-diphenylmethyl)pyrrolidine (0.6 g—see Preparation 8), 4-chlorophenethyl bromide (0.46 g), anhydrous potassium carbonate (0.6 g) and acetonitrile (20 ml) was heated under reflux for 1.25 hours. The mixture was partitioned between 10% aqueous potassium carbonate (10 ml) and dichloromethane (30 ml), the layers were separated, and the aqueous layer was extracted with dichloromethane (3×50 ml). The combined dichloromethane extracts were dried (MgSO$_4$) and concentrated in vacuo to Rive a foam which was purified by column chromatography on silica eluting with dichloromethane containing methanol (0% up to 6%). The product-containing fractions were combined and concentrated in vacuo to give the title compound as a foam, yield 0.43 g.

Analysis %: Found: C,74.14; H,6.58; N,6.33; Calculated for $C_{26}H_{27}ClN_2O$: C,74.53; H,6.50; N,6.69.

$^1$H-N.M.R. (CDCl$_3$) δ=7.50–7.05 (m, 15H); 5.50–5.40 (brs, 1H); 3.55–3.40 (m, 1H); 2.95–2.45 (m, 8H); 2.10–1.90 (m, 2H) ppm.

(B) A similar procedure starting with 3-(S)-(−)-(1-carbamoyl1,1-diphenylmethyl)pyrrolidine (0.64 g—see Preparation 10B) gave 3-(S)-(−)-(1-carbamoyl-1,1-diphenylmethyl)-1-(4-chlorophenethyl)pyrrolidine, yield 0.2 g, $[α]^{25}_D$−7.4° (c 1.0, CH$_2$Cl$_2$).

EXAMPLE 18

Preparation of 3-(S)-(1-carbamoyl-1,1-diphenylmethyl)-1-[2-(4-hydroxyphenyl)ethyl]pyrrolidine

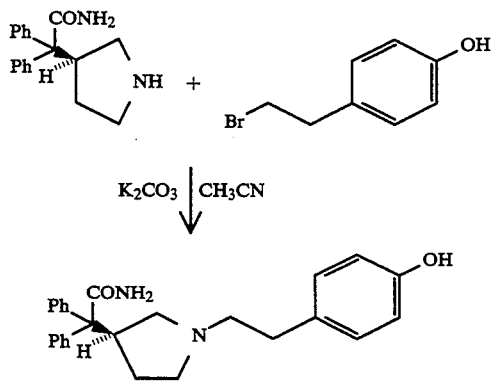

A mixture containing 3-(S)-(1-carbamoyl-1,1-diphenylmethyl)pyrrolidine (0.1 g—see Preparation 10B), 4-hydroxyphenethyl bromide (0.072 g), anhydrous potassium carbonate (0.15 g) and acetonitrile (2 ml) was heated under reflux for 45 minutes. On cooling, the mixture was partitioned between dichloromethane (5 ml) and 10% aqueous potassium carbonate (10 ml). The layers were separated, and the aqueous layer was further extracted with dichloromethane (2×5 m]). The combined dichloromethane extracts were dried (MgSO$_4$) and concentrated in vacuo to give a foam which was purified by column chromatography on silica eluting with dichloromethane containing methanol (5%). The product-containing fractions were combined and concentrated in vacuo to give the title compound as a colourless foam, yield 0.035 g.

Analysis %: Found: C,72.91; H,6.61; N,6.54; Calculated for $C_{26}H_{28}N_2O_2.H_2O.0.15\ CH_2Cl_2$: C,72.82; H,7.04; N,6.49.

$^1$H-N.M.R. (CDCl$_3$) δ=7.60–7.10 (m, 12H), 7.00–6.90 (d, 2H), 6.80–6.70 (d, 2H), 5.75–5.60 (brs, 1H), 3.55–3.45 (m, 1H), 2.95–2.85 (m, 2H), 2.85–2.60 (m, 5H), 2.15–1.90 (m, 2H) ppm.

EXAMPLE 19

Preparation of 3-(S)-(1-carbamoyl-1,1-diphenylmethyl)-1-[2-(4-acetylphenyl)ethyl]pyrrolidine

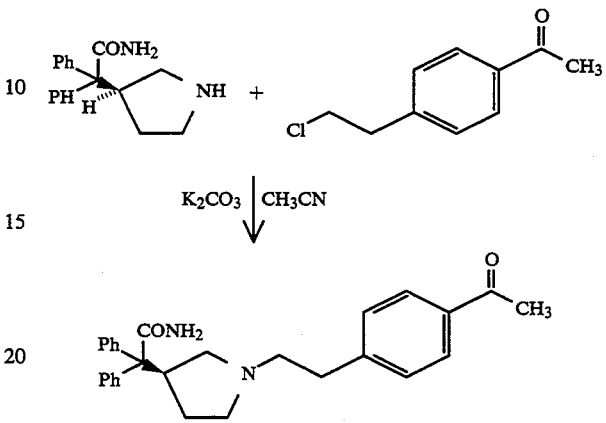

A mixture containing 3-(S)-(1-carbamoyl-1,1-diphenylmethyl)pyrrolidine (see Preparation 10B) (0.2 g), 4-acetylphenethy] chloride (0.142 g), anhydrous potassium carbonate (0.5 g) and acetonitrile (4 ml) was heated under reflux for 1 hour then allowed to cool to room temperature. The mixture was partitioned between dichloromethane (10 ml) and 10% aqueous potassium carbonate (20 ml). The layers were separated and the aqueous layer was further extracted with dichloromethane (2×10 ml). The combined dichloromethane extracts were dried (MgSO$_4$) and concentrated in vacuo to give an oil which was purified by column chromatography on silica eluting with dichloromethane containing methanol (2% up to 4%). The product-containing fractions were combined and concentrated in vacuo to give the title compound as a colourless glass, yield 0.05 g.

Analysis %: Found: C,73.78; H,6.92; N,6.05; Calculated for $C_{28}H_{30}N_2O_2.H_2O.1/6\ CH_2Cl_2$: C,73.74; H,7.10; N,6.10;

$^1$H-N.M.R. (CDCl$_3$) δ=7.95–7.85 (d, 2H), 7.45–7.20 (m, 13H), 5.50–5.40 (m, 1H), 3.65–3.50 (brm, 1H), 3.10–2.70 (m, 8H), 2.60 (s, 3H), 2.30–2.10 (brm, 1H), 2.10–1.95 (m, 1H) ppm.

The following Preparations illustrate the preparation of certain starting materials:

PREPARATION 1

Preparation of 3-(R)-(−)-hydroxypyrrolidine hydrochloride

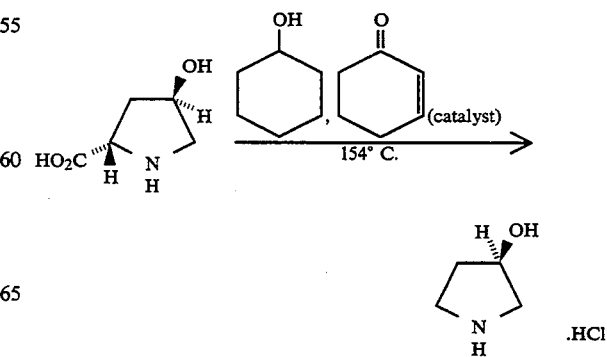

[See Chemistry Letters, 1986, 893.]

(2S,4R)-(—)-4-Hydroxy-2-pyrrolidinecarboxylic acid (40 g—commercially available), anhydrous cyclohexanol (200 ml) and 2-cyclohexen-1-one (2 ml) were heated together at 154° C. for 4.5 hours at which point the mixture was homogeneous. On cooling to room temperature, saturated ethanolic hydrogen chloride (150 ml) was added and the resulting crystalline solid was filtered off and washed with ethyl acetate (2×50 ml). The solid was recrystallised from isopropanol to give the title compound as colourless crystals, yield 19.15 g, m.p. 104°–108° C., $[\alpha]^{25}_D$ —8.0° (c 3.45, CH$_3$OH).

$^1$H N.m.r. (d$^6$DMSO), δ=10.00–8.60 (brs, 2H); 5.55–5.20 (brs, 1H); 4.40–4.25 (brs, 1H); 3.25–2.90 (m, 4H); 1.95–1.75 (m, 2H) ppm.

PREPARATION 2

Preparation of (R)-(—)-3-hydroxy-1-tosylpyrrolidine

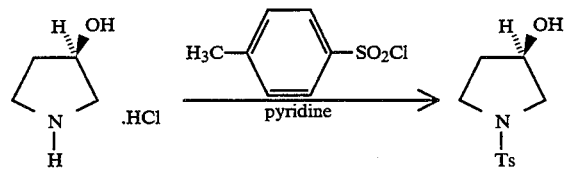

Para-toluenesulphonyl chloride (1.54 g) was added, in portions, to a solution of 3-(R)-(—)-3-hydroxypyrrolidine hydrochloride (1 g—see Preparation 1) in anhydrous pyridine (10 ml) at 0° C. The mixture was allowed to warm to room temperature and stirred for 16 hours. The solution was concentrated in vacuo and the residue was partitioned between dichloromethane (20 ml) and water (10 ml). The layers were separated and the aqueous layer was extracted with dichloromethane (2×15 ml). The combined dichloromethane extracts were washed with 2M hydrochloric acid (2×15 ml) and 10% aqueous sodium hydroxide (2×15 ml) then dried (MgSO$_4$) and concentrated in vacuo to give a solid which was recrystallised from ethanol to give the title compound as a colourless powder, yield 0.5 g, m.p. 108°–112° C., $[\alpha]^{25}_D$ —6.7° (c 1.0, CH$_2$Cl$_2$).

Analysis %: Found: C,54.69; H,6.23; N,5.78; Calculated for C$_{11}$H$_{15}$NO$_3$S: C,54.77; H,6.27; N,5.80.

$^1$H N.m.r. (CDCl$_3$), δ=7.80–7.70 (d, 2H); 7.40–7.30 (d, 2H); 4.45–4.35 (m, 1H); 3.50–3.35 (m, 3H); 3.30–3.25 (m, 1H); 2.45 (s, 3H); 2.05–1.80 (m, 2H); 1.75–1.70 (m, 1H) ppm.

PREPARATION 3

Preparation of 1-tosyl-3-(S)-(—)-tosyloxypyrrolidine

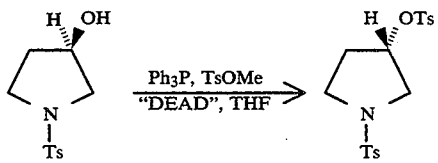

Methyl para-toluenesulphonate (54 g) was added in portions to solution of 1-tosyl-3-(R)-(—)-hydroxypyrrolidine (49 g—see Preparation 2) and triphenylphosphine (76 g) in anhydrous tetrahydrofuran (700 ml) at 0° C. The mixture was cooled to —20° C. and diethyl azodicarboxylate (58 g—"DEAD") was added, dropwise, over 30 minutes. During this time, the temperature of the mixture was not allowed to rise above —10° C. When the addition was complete the mixture was allowed to warm to room temperature and stirred for 16 hours. The mixture was concentrated in vacuo to give a solid which was purified by column chromatography on silica eluting with hexane containing dichloromethane (50%). The product-containing fractions were combined and concentrated in vacuo to give an oil which was crystallised from 1-propanol to give the title compound as a colourless solid, yield 56 g, m.p. 110° C., $[\alpha]^{25}_D$ —5.2° (c 1.0, CH$_2$Cl$_2$).

Analysis %: Found: C,54.62; H,5.46; N,3.14; Calculated for C$_{18}$H$_{21}$NO$_5$S$_2$: C,54.66; H,5.35; N,3.54.

$^1$H N.m.r. (CDCl$_3$), δ=7.75–7.65 (m, 4H); 7.40–7.30 (m, 4H); 5.00–4.90 (m, 1H); 3.55–3.35 (m, 3H); 3.30–3.20 (m, 1H); 2.50 (s, H); 2.45 (s, 3H); 2.10–1.90 (m, 2H) ppm.

PREPARATION 4

Preparation of 1-tosyl-3-(R)-(+)-tosyloxypyrrolidine

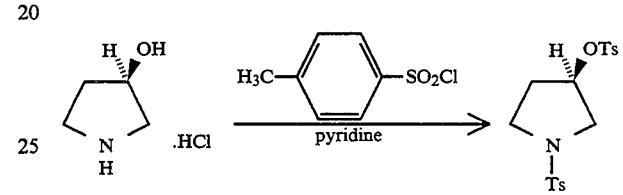

Para-toluenesulphonyl chloride (61.5 g) was added, in portions, to a solution of 3-(R)-(—)-3-hydroxypyrrolidine hydrochloride (19 g—see Preparation 1) in anhydrous pyridine (200 ml) at 0° C. The mixture was allowed to warm to room temperature and stirred for 16 hours. The solution was concentrated in vacuo and the resulting solid partitioned between dichloromethane (300 ml) and water (200 ml). The layers were separated and the aqueous layer extracted with dichloromethane (3×100 ml). The combined dichloromethane extracts were washed with 2M hydrochloric acid (2×100 ml) and 10% aqueous sodium hydroxide (2×100 ml) then dried (MgSO$_4$) and concentrated in vacuo to give an oil. Trituration with ether gave a solid which was recrystallised from 1-propanol to give the title compound as a colourless solid, yield 33.5 g, m.p. 111°–112° C. $[\alpha]^{25}_D$+5.3° (c 1.0, CH$_2$Cl$_2$).

Analysis %: Found: C,54.29; H,5.39; N,3.59; Calculated for C$_{18}$H$_{21}$NO$_5$S$_2$: C,54.68; H,5.35; N,3.54.

$^1$H N.m.r. (CDCl$_3$), δ=7.75–7.65 (m, 4H); 7.40–7.30 (m, 4H); 5.00–4.90 (m, 1H); 3.55–3.35 (m, 3H); 3.30–3.20 (m, 1H); 2.50 (s, 3H); 2.45 (s, 3H); 2.10–1.90 (m, 2H) ppm.

PREPARATION 5

Preparation of 1-tosyl-3-(R,S)-tosyloxypyrrolidine

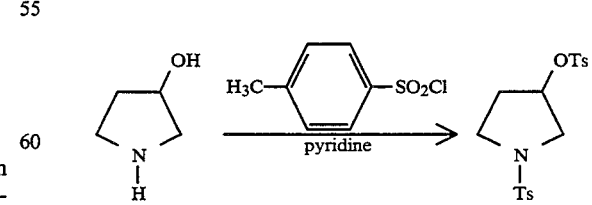

Para-toluenesulphonyl chloride (68.8 g) was added, in portions, to a solution of 3-(R,S)-hydroxypyrrolidine (15 g) in dry pyridine (200 ml) at 0° C. The mixture was allowed to warm to room temperature and stirred for 16 hours. The solution was concentrated in vacuo to approximately half the original volume then partitioned between dichloromethane (500 ml) and water (300 ml). The layers were separated and the aqueous layer was extracted with dichloromethane (3×100 ml). The combined dichloromethane extracts were washed with 2M hydrochloric acid (100 ml) and 10% aqueous sodium hydroxide (100 ml) then dried (MgSO4) and concentrated in vacuo to give an oil which was crystallised from dichloromethane/ether to give the title compound as a microcrystalline powder, yield 28.3 g, m.p. 119°–121° C.

$^1$H N.m.r. (CDCl$_3$) , δ=7.75–7.65 (m, 4H); 7.40–7.30 (m, 4H); 4.95 (m, 1H); 3.55–3.35 (m, 3H); 3.30–3.20 (m, 1H); 2.50 (s, 3H); 2.45 (s, 3H); 2.10–1.90 (m, 2H) ppm.

PREPARATION 6

(A) Preparation of 3-(R,S)-(1-cyano-1,1-diphenylmethyl)-1-tosylpyrrolidine

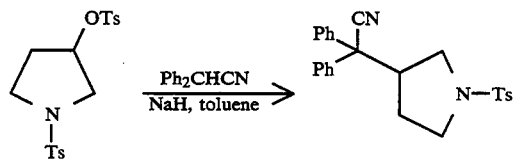

Diphenylacetonitrile (17.1 g) was added to a stirred suspension of sodium hydride (4 g of a 60% suspension in mineral oil) in anhydrous toluene (250 ml) and the mixture was heated under reflux for 2 hours. On cooling to room temperature, 1-tosyl-3-(R,S)-tosyloxypyrrolidine (28 g—see Preparation 5) was added in portions and the mixture heated under reflux for 3 hours. The mixture was diluted with toluene (150 ml), washed with 5% aqueous sodium hydroxide (2×100 ml) and brine (150 ml) then dried (MgSO4) and concentrated in vacuo to give a solid which was purified by trituration with methanol to give the title compound as a colourless microcrystalline powder, yield 18 g, m.p. 186°–187° C.

$^1$H N.m.r. (CDCl$_3$), δ=7.75 (d, 2H); 7.50–7.25 (m, 12H); 3.60–3.30 (m, 4H); 3.10–3.00 (m, 1H); 2.50 (s, 3H); 2.00–1.80 (m, 2H) ppm.

(B) A similar procedure starting with 1-tosyl-3-(S)-(−)tosyloxypyrrolidine (55 g—see Preparation 3) gave 3-(S)-(+)-(1-cyano-1,1-diphenylmethyl)-1-tosylpyrrolidine, yield 49.5 g, [α]$^{25}_D$+17.2° (c 1.0, CH$_2$Cl$_2$), m.p. 180°–185° C.

(C) A similar procedure starting with 1-tosyl-3-(R)-(+)-tosyloxypyrrolidine (33 g—see Preparation 4) gave 3-(R)-(−)-(1-cyano-1,1-diphenylmethyl)-1-tosylpyrrolidine, yield 19.7 g, m.p. 165°–178° C., [α]$^{25}_D$−17.0° (c 1.0, CH$_2$Cl$_2$).

PREPARATION 7

Preparation of 3-(R,S)-(1-cyano-1,1-diphenylmethyl)pyrrolidine

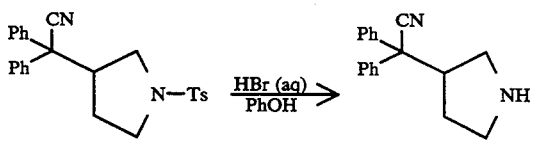

A solution of 3-(R,S)-(1-cyano-1,1-diphenylmethyl)-1-tosylpyrrolidine (21 g—see Preparation 6(A)) and phenol (21 g) in 48% aqueous hydrobromic acid (240 ml) was heated under reflux for 2 hours. The mixture was cooled to 0° C. in an ice bath and basified (pH 12) by the slow addition of 50% aqueous sodium hydroxide (280 ml). Methanol (10 ml) was added and the mixture was stirred for 15 minutes then diluted with water (300 ml). The mixture was extracted with dichloromethane (3×200 ml), the combined extracts were dried (MgSO4) and concentrated in vacuo to give an oil. The oil was dissolved in 1:1 hexane/toluene (500 ml) and washed with 0.5 M hydrochloric acid (3×500 ml). The aqueous extracts, together with some oil which separated during the extraction, were basified (pit 12) by the addition of aqueous sodium hydroxide (12 g in 20 ml water) and the mixture was extracted with dichloromethane (3×150 ml). The combined dichloromethane extracts were dried (MgSO4) and concentrated in vacuo to give an oil which was purified by column chromatography on silica eluting with dichloromethane containing methanol (0% up to 10%). The product-containing fractions were combined and concentrated in vacuo to give the title compound as a oil, yield 10 g.

$^1$H N.m.r. (CDCl$_3$), δ=7.55–7.25 (m, 10H); 5.45 (brs, 1H); 3.55–3.40 (m, 1H); 3.35–3.10 (m, 2H); 3.05–2.90 (m, 1H); 2.65–2.40 (m, 1H); 2.10–2.00 (m, 1H); 1.95–1.80 (m, 1H) ppm.

PREPARATION 8

Preparation of 3-(R,S)-(1-carbamoyl-1,1-diphenylmethyl)pyrrolidine

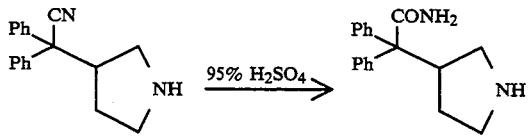

3-(R,S)-(1-Cyano-1,1-diphenylmethyl)pyrrolidine (30 g—see Preparation 7) was dissolved in 95% sulphuric acid (210 ml) and the mixture was heated, with stirring, at 85° C. for 9 hours and then at 100° C for 30 minutes. The mixture was allowed to cool to room temperature and poured onto ice (2 kg). The mixture was basified (pH 12) by addition, in portions with cooling in an ice bath, of a cold solution of sodium hydroxide (340 g) in water (500 ml). The resulting mixture was extracted with dichloromethane (3×300 ml) and the combined extracts were dried (MgSO4) and concentrated in vacuo to give the title compound as a foam, yield 16.4 g.

$^1$H N.m.r. (CDCl$_3$) δ=7.50–7.10 (m, 10H); 7.10–6.90 (brs, 0.5H); 5.90–5.30 (brm, 2.5H); 3.60–3.40 (m, 1H); 3.30–3.00 (m, 3H); 2.95–2.60 (m, 1H); 2.45–2.20 (m, 1H); 2.05–1.85 (m, 1H) ppm.

PREPARATION 9

(A) Preparation of 3-(S)-(+)-(1-cyano-1,1-diphenylmethyl)pyrrolidine

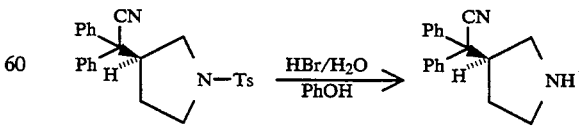

A mixture containing 3-(S)-(+)-(1-cyano-1,1-diphenylmethyl)-1-tosylpyrrolidine (49 g—see Preparation 6(B)), 48% aqueous hydrobromic acid (500 ml) and phenol (50 g) was heated under reflux for 1.25 hours then allowed to cool to room temperature. The mixture was extracted with ether (50 ml) to remove an upper layer of purple oil, then with 2:1 ether/hexane (150 ml). The aqueous layer was extracted with dichloromethane (4×100 ml), the dichloromethane extracts were combined, washed with 10% aqueous sodium hydroxide (3×50 ml), then dried (MgSO$_4$) and concentrated in vacuo to give an oil. The original ether extract was concentrated in vacuo to give an oil which was dissolved in dichloromethane (100 ml) and washed with 10% aqueous sodium hydroxide (3×50 ml). The dichloromethane solution was dried (MgSO$_4$) and concentrated in vacuo to give an oil which was combined with that obtained from the initial dichloromethane extraction. The combined oils were then dissolved in dichloromethane (200 ml) and washed with 10% aqueous sodium hydroxide solution (2×50 ml). The dichloromethane solution was dried (MgSO4) and concentrated in vacuo to give an oil which was purified by column chromatography on silica eluting with dichloromethane containing methanol (0% up to 10%). The product-containing fractions were combined and concentrated in vacuo to give the title compound as a foam, yield, 24.3 g, $[\alpha]^{25}_D +6.0°$ (c 1.0, CH$_2$Cl$_2$).

Analysis %: Found: C,78.09; H,6.70; N,9.93 Calculated for C$_{18}$H$_{18}$N$_2$.1/5 CH$_2$Cl$_2$: c,78.24; H,6.63; N,10.03.

(B) A similar procedure starting with 3-(R)-(−)-(1-cyano-1,1-diphenylmethyl)-1-tosylpyrrolidine (19.5 g—see Preparation 6(C)), gave 3-(R)-(−)-(1-cyano-1,1-diphenylmethyl)pyrrolidine, yield 9 5 g, $[\alpha]^{25}_D -9.8°$ (c 1.0, CH$_2$Cl$_2$).

PREPARATION 10

(A) Preparation of 3-(S)-(+)-(1-carbamoyl-1,1-diphenylmethyl)pyrrolidine L-(+)-tartrate

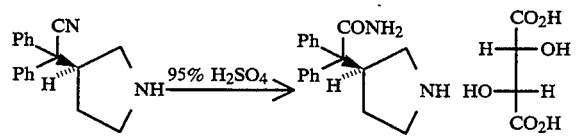

3-(S)-(+)-(1-Cyano-1,1-diphenylmethyl)pyrrolidine (24 g—see Preparation 9(A)) was dissolved in 95% sulphuric acid (210 ml) and the mixture was heated, with stirring, at 85° C. for 4.5 hours. The mixture was allowed to cool to room temperature and poured onto ice (500 g). The mixture was basified (pH 12) by the addition, in portions with cooling in an ice bath, of a cold solution of sodium hydroxide (335 g) in water (500 ml). The mixture was extracted with dichloromethane (4×200 ml) and the combined extracts were dried (MgSO$_4$) and concentrated in vacuo to give the free base of the title compound as a colourless foam, yield 8.5 g. A portion of the foam (5.5 g) was dissolved in ethanol (50 ml) and a solution of L-(+)-tartaric acid (3 g) in warm ethanol (30 ml) was added. The resulting solid was filtered off and recrystallised from methanol to give the title L-(+)-tartrate as colourless crystals, yield, 6 g, m.p. 180°–185° C., $[\alpha]^{25}_D +16.3°$ (c 1.0, H$_2$O).

Analysis %: Found: C,61.21; H,6.25; N,6.45; Calculated for C$_{18}$H$_{20}$N$_2$O.C$_4$H$_6$O$_6$: C,61.38; H,6.09; N,6.51.

$^1$H N.m.r. (d$^6$DMSO), δ=9.00–7.50 (brs, 4H); 7.40–7.10 (m, 11H); 6.90–6.80 (brs, 1H); 3.90 (s, 2H); 3.90–3.70 (m, 1H); 3.50–3.35 (m, 1H); 3.25–3.00 (m, 1H); 2.75–2.60 (m, 1H); 2.55–2.40 (m, 2H); 2.15–2.00 (m, 1H); 1.40–1.30 (m, 1H) ppm.

(B) Preparation of 3-(S)-(−)-(1-carbamoyl-1,1-diphenylmethyl)pyrrolidine

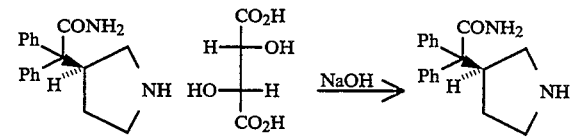

3-(S)-(+)-(1-Carbamoyl-1,1-diphenylmethyl)pyrrolidine L-(+)-tartrate from part (A) (0.95 g) was dissolved in water (40 ml) and basified (pH 12) by the dropwise addition of 10% aqueous sodium hydroxide. The mixture was extracted with dichloromethane (2×50 ml), the extracts were combined, dried (Na$_2$SO$_4$), and concentrated in vacuo to give the title compound as a colourless foam, yield 0.64 g.

$^1$H N.m.r. (CDCl$_3$) δ=7.50–7.20 (m, 11H); 6.35–6.20 (brs, 1H); 5.90–5.75 (brs, 1H); 3.55–3.45 (m, 1H); 3.25–3.10 (m, 2H); 3.05–2.95 (m, 1H); 2.95–2.85 (m, 1H); 2.15–2.05 (m, 1H); 1.90–1.80 (m, 1H) ppm.

PREPARATION 11

Preparation of 3-(R)-(+)-(1-carbamoyl-1,1-diphenylmethyl)pyrrolidine

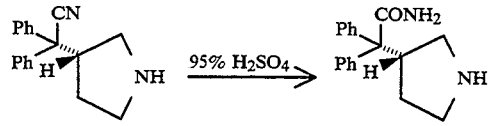

3 3-(R)-(−)-(1-cyano-1,1-diphenylmethyl)pyrrolidine (9.2 g—see Preparation 9(B)) was dissolved in 95% sulphuric acid (80 ml) and the mixture was heated at 80° C. for 4 hours and then at 90° C. for 1 hour. Ice (1 kg) was added and the mixture was basified (pH 12) by the addition of a cold solution of sodium hydroxide (120 g) in water (100 ml). The mixture was extracted with dichloromethane (4×100 ml) and the combined extracts were dried (MgSO$_4$) then concentrated in vacuo to give a foam which was purified by column chromatography on alumina eluting with dichloromethane containing methanol (0% up to 10%). The product-containing fractions were combined and concentrated in vacuo to give the title compound as a foam, yield, 4.5 g, $[\alpha]^{25}_D +16 9°$ (c 1.0, CH$_2$Cl$_2$).

$^1$H N.m.r. (CDCl$_3$), δ=7.45–7.20 (m, 10H); 6.10–5.90 (brs, 1H); 3.20–3.10 (m, 1H); 3.05–2.95 (m, 1H); 2.90–2.65 (m, 3H); 2.10–2.00 (m, 1H); 1.95–1.75 (m, 2H) ppm.

PREPARATION 12

N-[4-(2-methanesulphonyloxyethyl)phenyl]methanesulphonamide

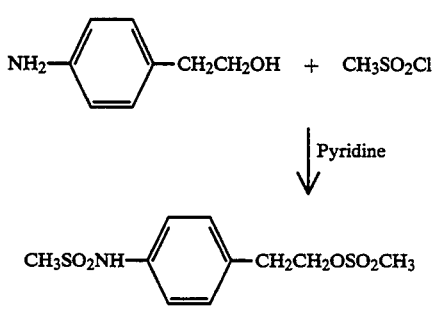

Methanesulphonyl chloride (50.4 g) was added dropwise to a stirred solution of 4-aminophenethyl alcohol (27.44 g) in dry pyridine (300 ml) at 0° and the solution was stirred at 0° for 30 minutes and then at room temperature for 2.5 hours. It was then poured into water and the solid was filtered off, washed with water, dried and crystallised from ethyl acetate to give the title compound (39.0 g, 66%), m.p. 136°–137°.

Analysis: %: Found: C,40.6; H,5.2; N,4.9; $C_{10}H_{15}NO_5S_2$ requires: C,40.9; H,5.1; N,4.8.

PREPARATION 13

Preparation of 4-carbamoylphenethyl bromide and 4-cyanophenethyl bromide

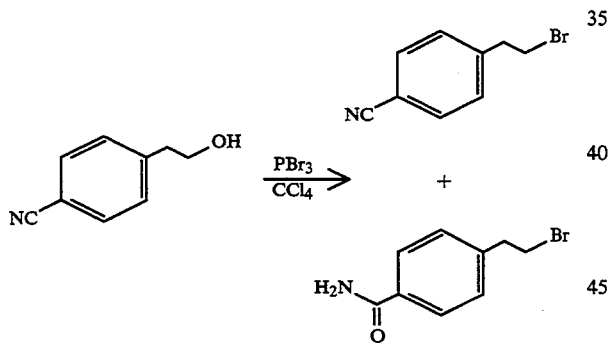

A solution of phosphorus tribromide (5 g) in carbon tetrachloride (10 ml) was added, dropwise, to a solution of 4-cyanophenethyl alcohol (8.06 g) in carbon tetrachloride (60 ml). The mixture was heated under reflux for 4 hours. On cooling to room temperature, the mixture was poured onto ice (200 g). The layers were separated and the organic layer was washed with 10% aqueous sodium carbonate (50 ml) and brine (50 ml), dried (MgSO₄) and concentrated in vacuo to give a colourless oil which solidified on standing. The solid was chromatographed on silica eluting with ethyl acetate containing hexane (20%). The fractions containing the less polar (higher $R_f$) product were combined and concentrated in vacuo to give 4-cyanophenethyl bromide as a yellow oil which solidified on standing, yield 8.9 g. The fractions containing the more polar (lower $R_f$) product were combined and concentrated in vacuo to give 4-carbamoylphenethyl bromide as a colourless solid, yield 0.47 g, m.p. 152°–153°.

PREPARATION 14

Preparation of 3,4-dichlorophenethyl bromide

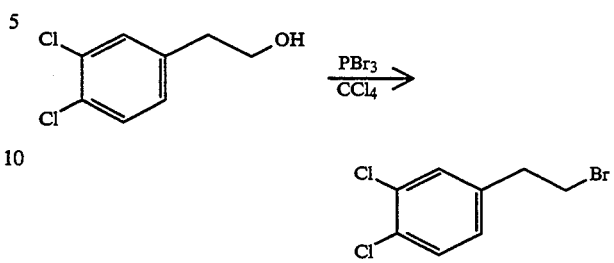

Phosphorus tribromide (2.17 g) was added, dropwise, to a solution of 3,4-dichlorophenethyl alcohol (4.26 g) in carbon tetrachloride (30 ml). The mixture was stirred at room temperature for 10 minutes then heated under reflux for 2 hours. 5% Aqueous sodium carbonate (10 ml) was added dropwise and the mixture was extracted with dichloromethane (3×70 ml). The combined dichloromethane extracts were dried (MgSO₄) and concentrated in vacuo to give a yellow oil which was purified by column chromatography on silica eluting with dichloromethane containing hexane (30% down to 0%). The product-containing fractions were combined and concentrated in vacuo to give the title compound as a colourless oil, yield, 1.8 g.

¹H-N.M.R. (CDCl₃) δ=7.50–7.30 (m, 2H); 7.15–7.05 (m, 1H); 3.65–3.50 (t, 2H); 3.20–3.10 (t, 2H) ppm.

PREPARATION 15

Preparation of methyl 4-(2-bromoethyl)benzoate

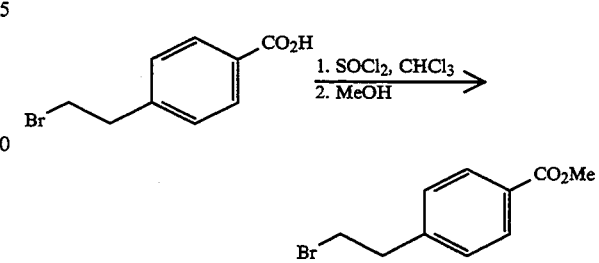

A solution of thionyl chloride (4.8 g) in chloroform (10 ml) was added, dropwise, to a solution of 4-(2-bromoethyl)benzoic acid (5.7 g) in chloroform (40 ml) and anhydrous dioxan (20 ml). When the addition was complete, the mixture was heated under reflux for 2 hours then cooled to room temperature and further thionyl chloride (2.4 g) in chloroform (10 ml) was added. The mixture was heated under reflux for 2 hours then allowed to cool to room temperature and concentrated in vacuo to give an oil which was dissolved in methanol (50 ml) and heated under reflux for 10 minutes. On cooling to room temperature, the mixture was stirred for 48 hours then concentrated in vacuo. The residue was parititoned between ethyl acetate (200 ml) and 5% aqueous sodium carbonate (200 ml), the layers were separated and the organic layer was washed with water (150 ml) then dried (MgSO₄) and concentrated in vacuo to give the title compound as an oil, yield, 5.7 g.

Analysis %: Found: C,49.64; H,4.60; Calculated for $C_{10}H_{11}BrO_2$: C,49.41; H,4.56.

¹H-N.M.R. (CDCl₃) δ=8.05–8.00 (d, 2H); 7.35–7.25 (d, 2H); 3.95 (s, 3H); 3.65–3.55 (t, 2H); 3.30–3.20 (t, 2H) ppm.

PREPARATION 16

Preparation of methyl 3,4-dimethylphenylacetate

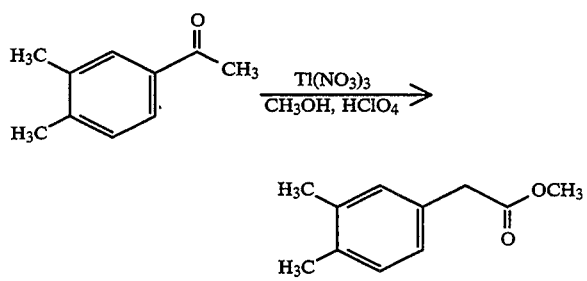

3,4-Dimethylacetophenone (4.59 g) was added to a solution of thallium (III) nitrate (13.75 g) in methanol (75 ml) and 70% perchloric acid (5 ml). The mixture was stirred at room temperature for 16 hours then filtered and the filtrate diluted with water (100 ml). The resulting cloudy solution was extracted with dichloromethane (3×100 ml). The combined dichloromethane extracts were dried (MgSO₄) and concentrated in vacuo to give an oil which was purified by column chromatography on silica eluting with hexane containing dichloromethane (25%). The product-containing fractions were combined and concentrated in vacuo to give the title compound as a colourless oil, yield, 3.0 g, which was used directly—see Preparation 17).

PREPARATION 17

Preparation of 3,4-dimethylphenethyl alcohol

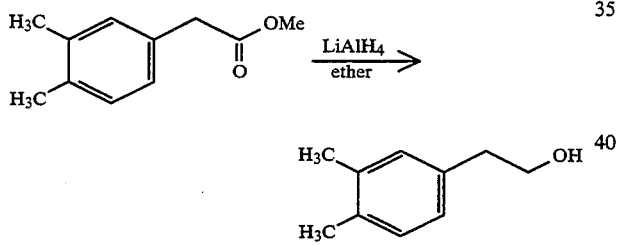

Lithium aluminium hydride (0.4 g) was added in portions to a solution of methyl 3,4-dimethylphenylacetate (3.0 g—see Preparation 16) in anhydrous diethyl ether (50 ml). When the addition was complete, the mixture was heated under reflux for 1 hour then allowed to stand at room temperature for 16 hours. Water (0.5 ml) was carefully added dropwise followed by 15% aqueous sodium hydroxide (0.5 ml) and finally more water (2 ml). The resulting solid precipitate was filtered off and washed with diethyl ether (3×20 ml). The filtrate and washings were combined, dried (MgSO₄) and concentrated in vacuo to give the title compound as a colourless oil which was used directly—see Preparation 18).

PREPARATION 18

Preparation of 3,4-dimethylphenethyl bromide

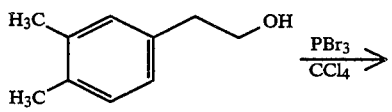

-continued

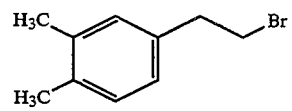

Phosphorus tribromide (0.82 g) was added dropwise to a solution of 3,4-dimethylphenethyl alcohol (1.27 g—see Preparation 17) in carbon tetrachloride (10 ml). The mixture was heated under reflux for 2.5 hours then cooled to room temperature and basified (pit 8) by the dropwise addition of 10% aqueous sodium carbonate (5 ml). The mixture was then diluted with water (20 ml) and extracted with dichloromethane (3×50 ml). The combined dichloromethane extracts were dried (MgSO₄) and concentrated in vacuo to give the title compound as a colourless oil, yield, 0.5g.

¹H-N.M.R. (CDCl₃) δ=7.20–6.95 (m, 3H); 3.65–3.55 (t, 2H); 3.20–3.10 (t, 2H); 2.30 (s, 3H); 2.25 (s, 3H) ppm.

We claim:

1. A compound of the formula:

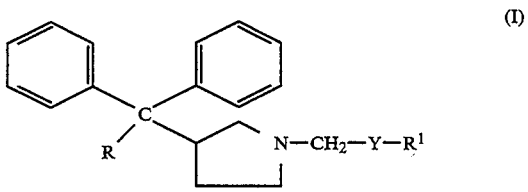

(I)

or a pharmaceutically acceptable salt thereof, wherein
Y is —CH₂—, —(CH₂)₂—, —CH₂O—, —(CH₂)₂O— or —CH₂S—;
R is —CONH₂; and
R¹ is a group of the formula:

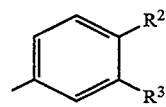

where
R² and R³ are each independently H, C₁–C₄ alkyl, C₁–C₄ alkoxy, —(CH₂)ₙOH, halo, trifluoromethyl, cyano, —(CH₂)ₙNR⁴R⁵, —CO(C₁–C₄ alkyl), —O-CO(C₁–C₄ alkyl), —CH(OH) (C₁–C₄ alkyl), —C(OH)(C₁–C₄ alkyl)₂, —SO₂NH₂, —(CH₂)ₙCONR⁶R⁷ or —(CH₂)ₙCOO(C₁–C₄ alkyl);
R⁴ is H or C₁–C₄ alkyl;
R⁵ is H, C₁–C₄ alkyl or C₁–C₄ alkylsulphonyl;
R⁶ and R⁷ are each independently H or C₁–C₄ alkyl; and
n is 0, 1 or 2.

2. A compound as claimed in claim 1 in which R² and R³ are each independently selected from H, halo, cyano, C₁–C₄ alkyl, C₁–C₄ alkoxy, C₁–C₄ alkoxycarbonyl, C₁–C₄ alkanesulphonamido, sulphamoyl, carbamoyl, hydroxymethyl, hydroxy and -CO(C₁–C₄ alkyl).

3. A compound as claimed in claim 2 in which Y is —CH₂—, —(CH₂)₂—, —CH₂O— or —(CH₂)₂O—.

4. A compound as claimed in claim 1 which is in the 3R,S-(racemic) or 3S- form.

5. Apharmaceutical composition comprising a compound of the formula (I) or pharmaceutically acceptable salt thereof as claimed in claim 1 and a pharmaceutically acceptable diluent or carrier.

6. A method of treating irritable bowel syndrome in a patient in need of such treatment, characterized by administering to said patient an effective amount of a compound of the formula

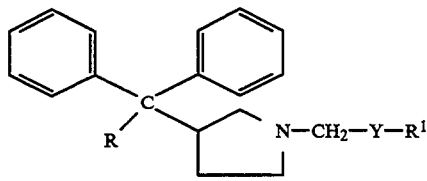
(I)

or a pharmaceutically acceptable salt thereof, wherein

Y is —CH$_2$—, —(CH$_2$)$_2$—, —CH$_2$O—, —(CH$_2$)$_2$O— or —CH$_2$S—;

R is —CN or —CONH$_2$; and

R$^1$ is a group of the formula:

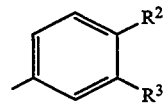

where

R$^2$ and R$^3$ are each independently H, C$_1$-C$_4$ alkyl, C$_1$-C$_4$ alkoxy, —(CH$_2$)$_n$OH, halo, trifluoromethyl, cyano, —(CH$_2$)$_n$NR$^4$R$^5$, —CO(C$_1$-C$_4$ alkyl), —O-CO(C$_1$-C$_4$ alkyl), —CH(OH)(C$_1$-C$_4$ alkyl), —C-(OH)(C$_1$-C$_4$ alkyl), —OCO(C$_1$-C$_4$ alkyl), —CH-(OH)(C$_1$-C$_4$ alkyl), —C(OH)(C$_1$-C$_4$ alkyl)$_2$, —SO$_2$NH$_2$, —(CH$_2$)$_n$CONR$^6$R$^7$ or —(CH$_2$)$_n$COO(C$_1$-C$_4$ alkyl);

R$^4$ is H or C$_1$-C$_4$ alkyl;

R$^5$ is H, C$_1$-C$_4$ alkyl or C$_1$-C$_4$ alkylsulphonyl;

R$^6$ and R$^7$ are each independently H or C$_1$-C$_4$ alkyl; and n is 0, 1 or 2.

* * * * *